United States Patent
Flinchbaugh

Patent Number: 5,114,412
Date of Patent: May 19, 1992

[54] MAGNETIC BLADDER CYCLER

[76] Inventor: David E. Flinchbaugh, 4855 Big Oaks La., Orlando, Fla. 32806

[21] Appl. No.: 401,434

[22] PCT Filed: Nov. 7, 1988

[86] PCT No.: PCT/US88/03929
§ 371 Date: Apr. 20, 1989
§ 102(e) Date: Apr. 20, 1989

[51] Int. Cl.⁵ .............................. A61M 5/00
[52] U.S. Cl. .................. 604/247; 128/DIG. 25; 251/65
[58] Field of Search .................. 604/8-10, 604/118, 129, 247; 128/DIG. 25; 600/29, 30; 251/65

[56] References Cited

U.S. PATENT DOCUMENTS

| | | | |
|---|---|---|---|
| 2,667,895 | 2/1954 | Pool et al. | 251/65 |
| 3,105,511 | 10/1963 | Murphy | 251/65 |
| 3,495,620 | 2/1970 | Raimondi et al. | 251/65 |
| 3,731,670 | 5/1973 | Loe | 128/DIG. 25 |
| 4,424,058 | 1/1984 | Parsons et al. | 604/247 |
| 4,425,123 | 1/1984 | Di Salvo | 604/247 |
| 4,705,070 | 11/1987 | Eidsmore | 251/65 |

Primary Examiner—Max Hindenberg
Attorney, Agent, or Firm—Steven J. Hultquist

[57] ABSTRACT

A bladder cycler is provided with a magnetic valve for hospital, clinical and home-care use in emptying of the bladder of a patient through a catheter. Fully automatica or automatic with manual override operation are provided for opening and closing a valve to empty the bladder of urine when necessary.

12 Claims, 2 Drawing Sheets

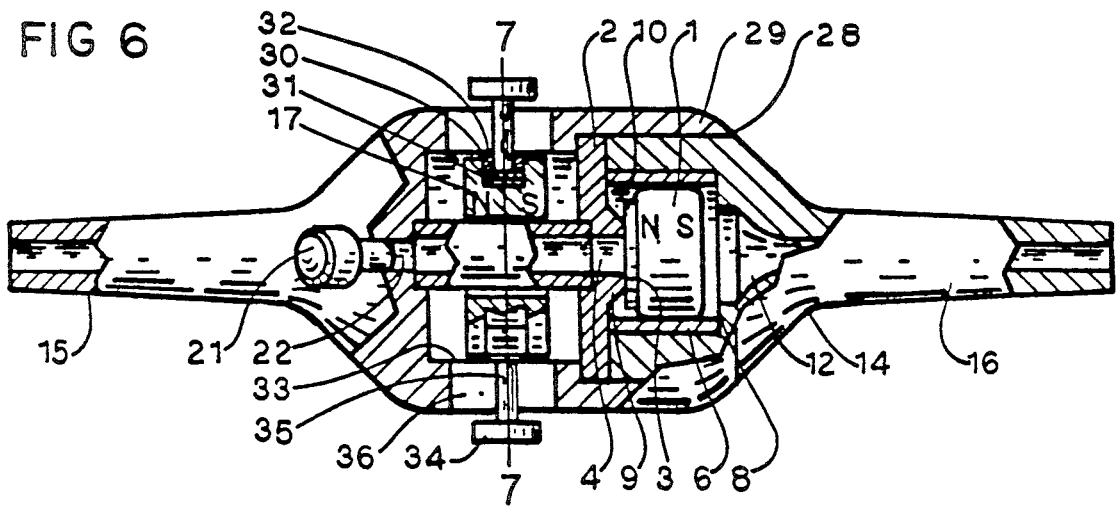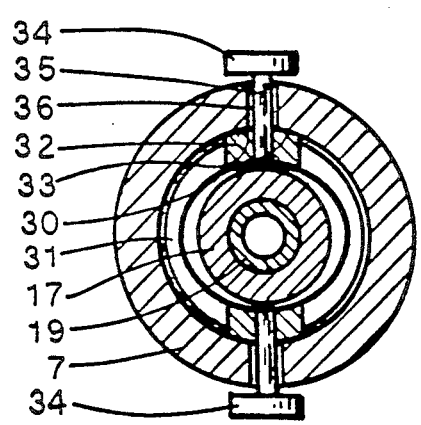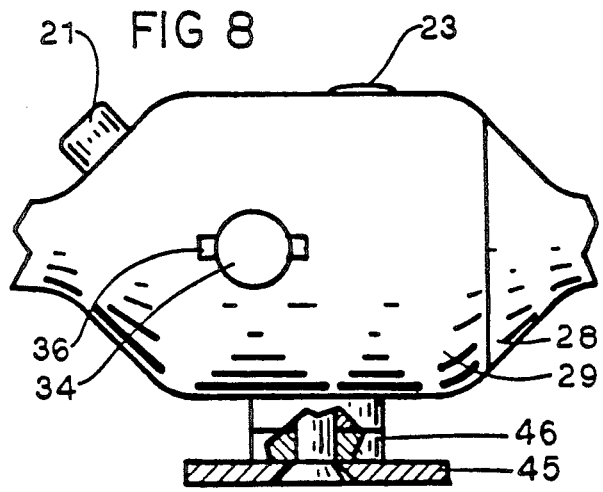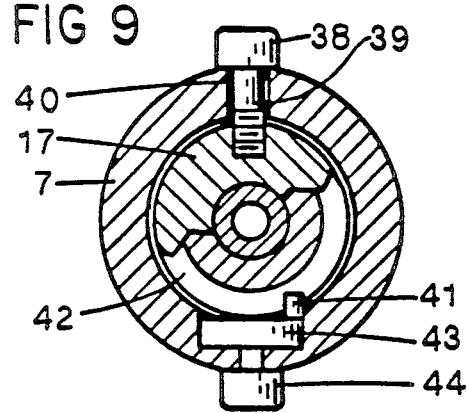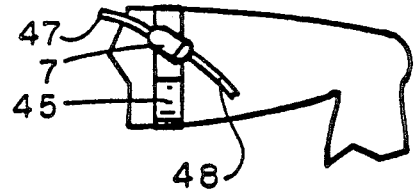

MAGNETIC BLADDER CYCLER

BACKGROUND OF THE INVENTION

1. Technical Field

This invention relates to a bladder drainage cycler and method of use. It is a hospital, clinical or home-care medical instrument for draining urine from bladders of patients automatically, thoroughly and antiseptically when necessary to bypass natural bladder drainage.

2. Background Information

Hospital instruments and procedures for draining bladders of patients has evolved from constant uncycled drainage through siphoning, suction and various types of cyclic methods. Fundamental to an effective instrument and method is allowing the bladder to fill reasonably and then draining it without a suction effect and without allowing build-up or entry of infectious contaminants in the drainage system.

Included in previous methods have been U.S. Pat. Nos. 2,602,448 and 2,860,636 which utilized a siphon in combination with a reservoir to provide cyclic draining of the bladder. Pressure release in these is controlled by raising the height of the device on a bedside tree. It is subject to distortion by shifting and turning of the patient and therefore, very undependable in addition to being restrictive of the patient.

In U.S. Pat. No. 3,598,124, a siphon leg is controlled by merely attaching a catheter to a bedside tree at predetermined adjusted height, which varies the pressure at which the bladder will drain and provides a flutter valve near the patient to break the siphon action of the system once the bladder has drained. In U.S. Pat. No. 4,230,102, a device for the draining of a bladder is shown in which a T-joint has been placed on a catheter and has a pressure membrane attached thereto in a large casing for actuating a pressure switch which in turn actuates an electric motor driving a gear train and cam. A cam follower is spring loaded to close the catheter for two minute cycles upon actuation by the pressure switch to drain the bladder. This type of device, however, is expensive and bulky and positions an electrical apparatus adjacent to the catheter. In U.S. Pat. No. 4,424,058, a spring-return valve is provided in conjunction with a siphon-release orifice to prevent excessive suction and to prevent urine from remaining in the system after drainage. A problem with this system was that resistance of the spring increased with distance of travel from a closed position. This tended to cause some fluid to remain in the bladder because only a full bladder would open it and only a relatively full bladder would keep it open to allow complete drainage unless overriden by the patient. Also, positioning of tubes leading from it were parallel to the leg on which it was attached and provided a situation for retention of fluid in the system.

This invention provides magnetic closing of a valve member with decreased rather than increased closing pressure when opened. As the bladder is emptied, decreasing head pressure against the valve, therefore, can keep the valve open for more complete drainage than can be provided by a resiliency-operated valve.

Valve-closing pressure decreases as a result of three factors: (1) magnetic pull of a valve decreases as its open distance from magnetic attraction in the direction of a valve seat increases, (2) fluid passing through the system provides a partial insulation which tends to decrease magnetic attraction between magnetic members, and (3) an optional spring in one of the embodiments of the invention causes the magnetic members to be further apart when the valve opens.

In addition, one of the embodiments of the invention provides convenient manual override to decrease or eliminate totally the magnetic closing pressure of the valve.

SUMMARY OF THE INVENTION

A bladder drainage wafer valve member is magnetically attracted towards a valve-port wall. Head pressure of urine in a bladder and in a drainage tube from the bladder to the valve where it is positioned on a patient's leg causes the valve to open away from the valve-port wall. When the valve is opened, distance increases between the valve member and a member to which it is magnetically attracted in the direction of the valve-port wall. An optional spring moves the member to which it is attracted yet further away and further decreases the magnetic attraction, thereby allowing the valve to remain open with less pressure than required to open it. Fluid passing between the open valve and the member to which it is attracted magnetically decreases further yet the closing pressure to offset the head-pressure opening of the valve.

Downstream from the valve, there is a siphon-release air-inlet orifice that relieves siphon pressure to avoid siphon suction that would either cause collapse of the bladder walls or cause the valve to remain open after the bladder is emptied. An air inlet to the siphon-release orifice is positioned upstream and radially outward from an outlet to the valve in order to prevent passage of fluid from the valve where siphon pressure does not provide sufficient inward suction of air. The siphon-release orifice is provided with an antiseptic strainer and a low-pressure one-way inlet valve.

Optional embodiments of this invention provide manual override of the valve by selective distancing of a magnetic member from the valve member that is attracted to it. This gives flexibility of pressure adjustment and provides the opportunity of assuring full drainage when desired.

A swivelable attachment of the bladder cycler to a strap on a patient's leg allows it to be positioned at a slant with the outlet and tubes leading from it downward from the valve to further assure that fluid will not remain in the system between drainage cycles whether used in either a prone or vertical position of the leg.

BRIEF DESCRIPTION OF THE DRAWINGS

The objects, features and advantages of this invention will be apparent from the written description of the drawings in which:

FIG. 6 is a cutaway side view of a variable control embodiment of this invention;

FIG. 7 is a cross-section view designated as through position DD in FIG. 6;

FIG. 8 is a cutaway side view of the variable control embodiment shown in FIG. 6;

FIG. 9 is a sectional cutaway end view of two separate means for controlling the head pressure required to open the valve in the embodiment of the invention illustrated in FIG. 6;

FIG. 10 is a side view of a patient's leg with either embodiment strapped to it in a slanted position.

DESCRIPTION OF PREFERRED EMBODIMENTS

Figure 1:
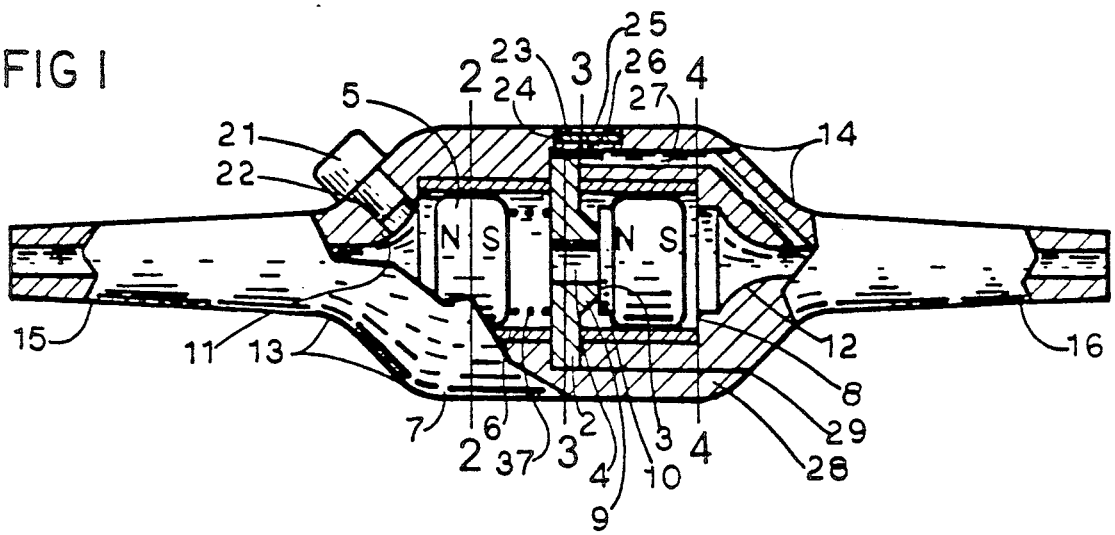
FIG. 1 is a cutaway side view of a fully automatic drainage embodiment of this invention.

Referring to FIG. 1, a magnetic valve member 1 is magnetically attracted in the direction of valve-port wall 2 having valve seat 3 at an outlet end of valve orifice 4. The magnetic valve member can be attracted magnetically to either the valve-port wall or to an upstream magnetic member 5. Magnetic attraction can be provided by composition of either or both the valve member and the upstream magnetic member. Optionally and preferably, the magnetic valve member and the upstream magnetic member both are magnetic and the valve-port wall is non-magnetic. When either the valve-port wall or the magnetic base member have magnetic force and the magnetic valve member also has magnetic force, opposite poles of each are facing each other.

Figure 2:
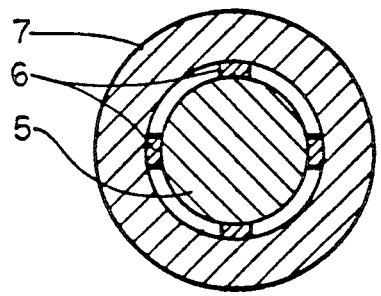
FIG. 2 is a cross-section view designated as 2'2' through position 2—2 in FIG. 1.
Figure 3:
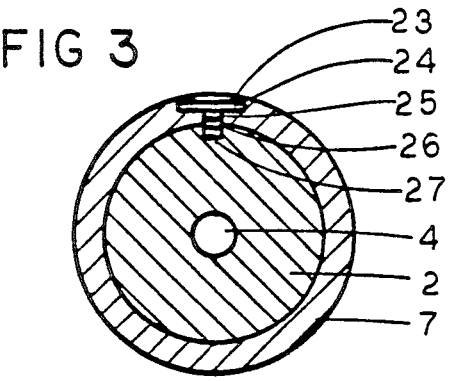
FIG. 3 is a cross-section view designated as 3'3' through position 3—3 in FIG. 1.

Referring to FIGS. 1, 2 and 6, channel ridges 6 at the inside periphery of non-magnetic housing 7 provide fluid passage linearly between them from side-to-side of first the magnetic base member and then the magnetic valve member.

Figure 4:
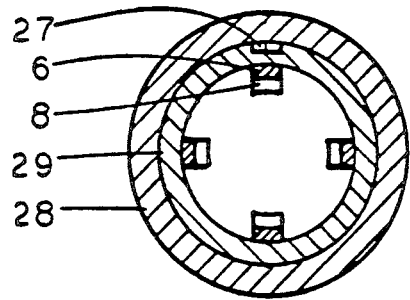
FIG. 4 is a cross-section view designated as 4'4' through position 4—4 in FIG. 1.
Figure 5:
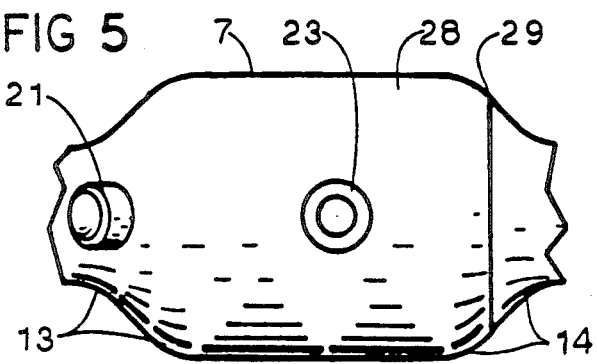
FIG. 5 is a top view of the center section of FIG. 1.

Referring to FIGS. 1, 4 and 6, stopper shoulders 8 are provided to arrest travel of the magnetic valve member at a select distance of travel from the valve-port wall.

Referring to FIGS. 1 and 6, the valve-port wall is provided with an optional valve-seat ridge 9 for reduction of valve-seat area to reduce area for accumulation of particulates in fluid passing through the system and for providing a relatively smaller surface for tightly seating into the valve member. A resilient non-magnetic valve surface 10 can be provided for increased seating pressure and for selectively decreased magnetic attraction in the direction of the valve-port wall.

Referring to FIGS. 1 and 6, inside corners of magnetic valve members, inside corners of housing inlets 11, inside corners of housing outlets 12 and all other corners possible can be rounded to facilitate flow through the system and to prevent accumulation of particulates in fluid passing through the system. Outside inlet corners 13 and outlet corners 14 also can be rounded to prevent scraping action that would tend to accumulate particles at the outside and decrease cleanliness. In addition to being rounded, the inside corners of the housing outlets can be angled from the inlet connectors 15 and the outlet connectors 16 which can be selectively tapered, ribbed or otherwise designed to receive and to hold medical tubing.

Referring to FIGS. 1 and 6, all components downstream to the right, starting with the valve-port wall at a position designated as BB in FIG. 1, can be the same for both embodiments illustrated, except for size modifications and, therefore, are numbered the same for both.

Referring to FIGS. 6 and 7 upstream from the valve-port wall, a positionable magnetic base member 17 with inside periphery of a bearing orifice 18 is in slidable contact with the outside periphery of bearing tube 19 which is extended between housing inlet aperture 20 and the valve orifice in the valve-port wall.

Referring to FIGS. 1, 5, 6 and 8, medicine can be inserted into the bladder and into the bladder cycler upstream from the valve member by removal of an insertion plug 21 in insertion orifice 22.

Referring to FIGS. 1, 3, 5, 6 and 8, a siphon air vent cover 23 can be provided to hold and to protect a strainer 24 at the outside of vent inlet orifice 25. A low-pressure vent valve 26 is opened inwardly into vent aperture 27 with siphon suction negative pressure from fluid passing through the housing outlets. This feature of the invention can be the same for both embodiments illustrated.

Typically for construction purposes, the vent valve can be positioned at the outside periphery of a valve-port wall and the vent aperture can be positioned in the outside periphery of an outlet housing member 28 that is insertable during construction assembly into an inlet housing member 29 after first inserting the magnetic valve members and the valve-port wall. The assembly can be either glued or fit snugly enough to remain assembled without glue.

Referring to FIGS. 6, 7 and 8, variability of pressure or elimination of pressure to open the valve is provided by selective manual positioning of a positional magnetic base member in this embodiment of the invention. There are a variety of methods that can be employed to position this magnetic base member manually and cause it remain where positioned until moved again as desired. One method can be with the use a circular control spring 30 in a control channel 31 circumferentially around the outside periphery of the magnetic base member. Traction members 32 in the control channel at opposite sides of the bladder cycler are pressured outward radially against the insider periphery 33 of the housing by the spring. This provides traction to hold the magnetic base member where positioned. Then to move the magnetic base member to a position closer to or farther from the magnetic valve member, the pressure of the spring against the inside periphery of the housing is overcome by pressing a control button 34 at each side of the cycler. The control buttons are connected to control stems 35 which are connected to the traction members, such that a finger and a thumb at opposite sides of the cycler can be used to relieve the traction pressure and re-position the positionable magnetic base member conveniently. The control stems can travel linearly in stem apertures 36.

The traction member and the spring can be constructed of non-magnetic materials and the spring can be formed of non-metallic resilient material. The traction spring is held in an elliptical form by the thickness of the traction members between the inside periphery of the housing and the outside periphery of the resilient member or ring-shaped control spring. Outward pressure of the spring tending to become circular can be relieved and thus relieve traction pressure against the inside periphery of the housing when the buttons are both pressured inwardly. Balancing of pressure of two fingers, one at each side of the cycler, does not move the cycler when so utilized.

Head pressure to open the valve is decreased by pressing the button inwardly and sliding the magnetic base member in the direction of the housing inlet. The valve is totally released without any magnetic pressure to hold the valve shut when the magnetic base is slid to the extreme housing-inlet end of travel of the button stem in the stem channels. Closing pressure of the valve is increased by sliding the magnetic base member in a downstream direction toward the housing outlet.

The magnetic base member never comes in contact with fluid in the system because there is sealing at both ends of the bearing tube. There is no need for rounded edges of the inlet nor of the magnetic base member in this override embodiment of the invention.

Referring to FIG. 1, the magnetic base member can be either glued or otherwise fixed in a position at a select distance from the valve-port wall to achieve a pre-determined pressure requirement for opening of the valve in opposition to magnetic attraction of the base member and the valve. Alternatively, however, the magnetic base member in FIG. 1 can be moveable by an automatic drainage spring or other resilient member 37. When pressure from the weight of fluid in the bladder and in the column from the bladder to the bladder cycler cause the valve to open in opposition to the magnetic attraction, the spring will cause the base member to move upstream away from the valve member and thereby decrease further the attraction between the two magnets. This allows more complete emptying of the bladder contents. Although not manually-controllable, this embodiment of the invention provides some features of the controllable embodiment at a lower cost of construction. A spring in this working relationship functions in the opposite direction as springs used to close valves in prior-art practices. It decreases rather than increases opening pressure of the valve when pressure in the bladder is low from being partially emptied.

Referring to FIG. 9, two alternative means are shown for controlling the head pressure required to open the valve in the embodiment of the invention illustrated in FIG. 6. They can be employed separately or together. Therefore, they are shown in the same drawing figure. One is comprised of a bolt knob 38 with bolt stem 39 that is threadable into the magnetic base member for creating resistance pressure against the outside periphery of the housing. The stem of the bolt would be slidable in a bolt aperture 40 similar to the apertures shown for sliding the two button stems.

The other head-pressure control means is an offset cam-follower member 41 which is inserted in a channel 42 similar to the channel in which the ring-shaped spring is positioned in the magnetic base member. The offset member is attached to cam-follower wheel 43 which is rotatable by rotational control knob 44 to cause the magnetic base member to travel linearly.

Referring to FIGS. 8 and 10, a leg strap 45 is provided with a swivel connection 46 that allows the bladder cycler to be positioned when desired at a downward angle with respect to a leg to which is attached. This allows a catheter or drainage tubing 47 and outlet tubing 48 to be positioned at a slant that provides downward flow of fluid that otherwise could remain in the system between drainage cycles.

What is claimed is:

1. A magnetic bladder cycler comprising:
   a non-magnetic tubular housing;
   a non-magnetic tubular inlet conveyance positioned concentrically to the axis of an inlet end of the tubular housing;
   a non-magnetic tubular outlet conveyance positioned concentrically to the axis of an outlet end of the tubular housing;
   a valve-port well positioned stationary within the tubular housing between the inlet and outlet ends thereof and having a valve orifice concentric to the axis of the tubular housing.
   a valve member having an outside periphery greater than the inside periphery of the valve orifice in slidable contact with the portions of the inside periphery of the housing and positioned between the valve-port wall and the outlet end of the tubular housing;
   selective magnetic attraction of the valve member in the direction of the orifice in the valve-port wall;
   a siphon-vent orifice positioned in the outlet end of the tubular housing;
   a upstream magnetic member in slidable contact with portions of the inside periphery of the housing selectively upstream from the valve-port wall within the housing;
   a magnetic valve member with a magnetic pole facing in the direction of an opposite magnetic pole of the upstream magnetic member; and
   a resilient member with selective expansion pressure between the upstream magnetic member and the valve-port wall such that the upstream magnetic member is slidable further upstream and magnetic attraction between the two magnetic members is decreased further when the two magnetic members are separated by pressure from fluid mass and tissue resistance within the bladder and resistance to flow of fluid from the bladder during bladder-drainage cycles is minimized.

2. A bladder cycler in accordance with claim 1 and further comprising:
   an upstream abutment positioned selectively upstream from the upstream magnetic member within the housing;
   upstream abutment fluid passageways in communication between the inlet to the housing and fluid passageways at the inside periphery of the housing in fluid communication between the upstream abutment fluid passageways and the upstream side of the valve-port wall;
   a downstream abutment positioned selectively downstream from the magnetic valve member within the housing; and
   downstream abutment fluid passageways in communication between the outlet to the housing and fluid passageways at the inside periphery of the housing in fluid communication between the downstream abutment fluid passageways and the downstream side of the valve-port wall.

3. A bladder cycler in accordance with claim 2 and further comprising:
   selectively rounded edges on the upstream magnetic member, the upstream abutment, the upstream fluid passageways, the upstream inlet conveyance, the magnetic valve member, the downstream abutment, the downstream fluid passageways and the downstream outlet conveyance.

4. A bladder cycler in accordance with claim 3 and further comprising:
   a sealable antibiotic input orifice in the housing upstream from the upstream magnetic member.

5. A bladder cycler in accordance with claim 4 and further comprising:
   a fluid conveyance in communication between a siphon-vent orifice positioned at a fluid outlet orifice at the outlet end of the tubular housing and a position outward radially and upstream linearly therefrom.

6. A bladder cycler in accordance with claim 5 wherein:

the siphon-vent orifice is large enough to allow entry of only a sufficient amount of air to avoid siphon effect of fluid in communication between a terminus of a conveyance and the outlet end of the housing but not large enough to allow passage of a sufficient amount of fluid through the siphon-vent orifice to prevent a suction effect of fluid traveling in a direction of least resistance to a lower elevation through an outlet conveyance attached to the outlet end of the tubular housing.

7. A bladder cycler in accordance with claim 6 and further comprising:

selectively magnetic insulative resilient material attached to the surface of the slidable valve member such that magnetic contact between the valve member and the wall is determined selectively thereby and a selectively tight sealing surface is formed between the insulative resilient material and the valve-port wall.

8. A bladder cycler in accordance with claim 7 and further comprising:

a selectively small circumferential surface area of the valve-port wall in contact with the magnetic valve member such that the selectively small surface area of contact of the wall and the valve member allows selectively small area onto which particulates in fluid passing between them can accumulate and magnetic attraction between the upstream magnetic member and the magnetic valve member causes the selectively small surface area of the valve-port wall to be pressured into the resilient material for maximized sealing effect.

9. A bladder cycler in accordance with claim 8 and further comprising:

a strainer material attachable to an inlet orifice of the siphon vent conveyance.

10. A bladder cycler in accordance with claim 9 and further comprising:

rounded outside edges of the outside periphery of the housing and the inlet and outlet conveyances such that clothing, linen, human flesh and other materials are not cut and scraped and portions thereof accumulated with infestation effects at the outside surfaces of the bladder cycler.

11. A bladder cycler in accordance with claim 10 and further comprising:

a selectively-swivelable means for attachment of the housing to a let of a person using the bladder cycler.

12. A bladder cycler in accordance with claim 11 and further comprising:

an outlet conveyance having an outside periphery shaped and sized to be inserted into and held snugly by the inside diameter of medical tubing in fluid communication between the outlet conveyance and a bladder fluid collector; and an inlet conveyance having an outside periphery shaped and sized to be inserted into and held snugly by the inside diameter of medical tubing in fluid communication between the inlet conveyance and a tubular attachment portion of a bladder drainage tube.

* * * * *